United States Patent
Pedersen et al.

(10) Patent No.: US 7,247,857 B2
(45) Date of Patent: Jul. 24, 2007

(54) METHOD AND AN APPARATUS FOR DETECTING WATER ON A SHIP'S DECK

(75) Inventors: Hald Niels Pedersen, Hvidovre (DK); Kjeld Dittmann, Gentofte (DK)

(73) Assignees: Force Technology, Brondby (DK); Lyngso Marine A/S, Horsholm (DK)

( * ) Notice: Subject to any disclaimer, the term of this patent is extended or adjusted under 35 U.S.C. 154(b) by 0 days.

(21) Appl. No.: 10/548,512

(22) PCT Filed: Mar. 12, 2004

(86) PCT No.: PCT/DK2004/000161

§ 371 (c)(1),
(2), (4) Date: Apr. 13, 2006

(87) PCT Pub. No.: WO2004/081551

PCT Pub. Date: Sep. 23, 2004

(65) Prior Publication Data

US 2006/0226369 A1    Oct. 12, 2006

(30) Foreign Application Priority Data

Mar. 14, 2003 (DK) ................................ 2003 00387

(51) Int. Cl.
*G01T 3/08* (2006.01)

(52) U.S. Cl. ............... 250/370.05; 250/357.1; 250/390.05; 250/390.01; 250/393; 250/390.11

(58) Field of Classification Search ........... 250/390.05, 250/357.1, 364, 370.05, 363.01, 390.01, 250/390.11, 393, 392
See application file for complete search history.

(56) References Cited

U.S. PATENT DOCUMENTS

| | | | |
|---|---|---|---|
| 3,716,711 A | 2/1973 | Olesen | |
| 4,646,068 A | 2/1987 | Skala | |
| 4,870,287 A | 9/1989 | Cole et al. | |
| 5,446,288 A | 8/1995 | Tumer | |

FOREIGN PATENT DOCUMENTS

GB    1 073 443    6/1967

*Primary Examiner*—David Porta
*Assistant Examiner*—Jessica Eley
(74) *Attorney, Agent, or Firm*—Day Pitney LLP

(57) ABSTRACT

This invention relates to an apparatus for detecting hydrogeneous material on a ship's deck comprising a neutron source located below the surface of the ship's deck and emitting fast/energy-rich neutrons, and a detector device that is located below the surface of the ship's deck and detecting thermal neutrons. The invention further relates to a corresponding method of detecting hydrogeneous material on a ship's deck. Hereby an apparatus and a method are provided for detecting occurrences of water on a ship's deck, wherein these occurrences appear in particular when travelling in rough weather conditions. The apparatus being located below the ship's deck, it is consequently not exposed to wear due to rough weather conditions.

10 Claims, 3 Drawing Sheets

Figure 1:
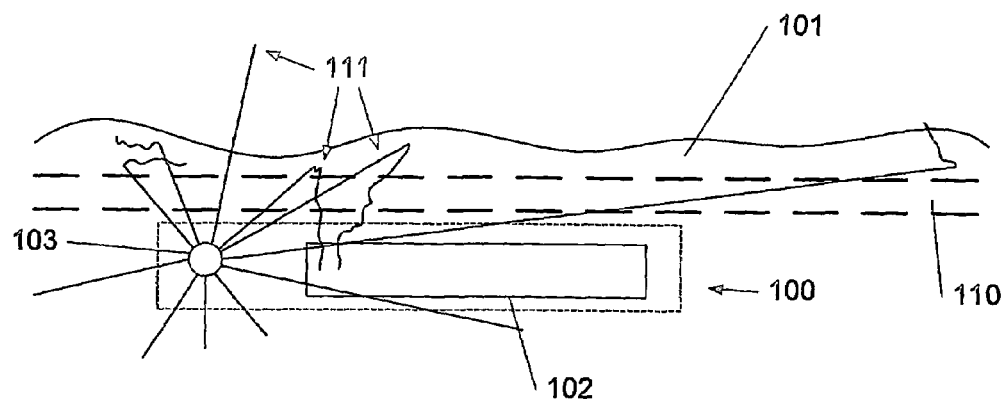

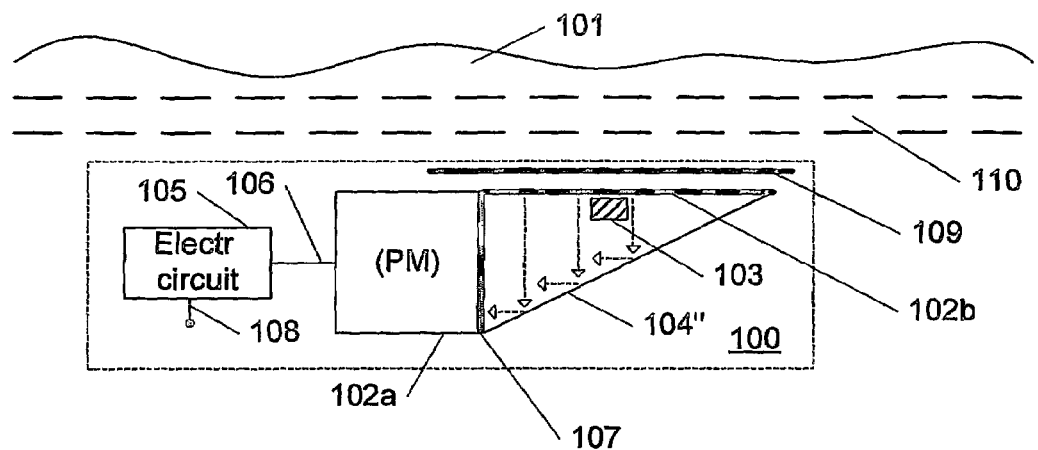
Fig. 2b
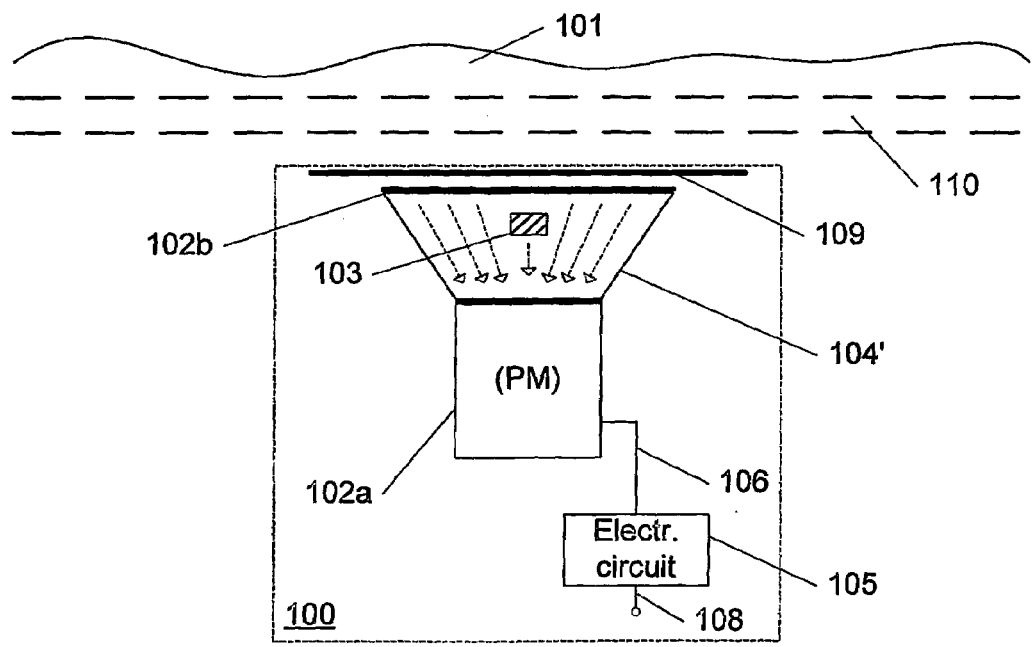
Figur 2c

METHOD AND AN APPARATUS FOR DETECTING WATER ON A SHIP'S DECK

The present invention relates to an apparatus for detecting water on a ship's deck. The invention also relates to a method of detecting water on a ship's deck. Finally, the invention relates to use of the apparatus according to the invention for detecting water that is present on the ship's deck.

When sailing in rough weather conditions, e.g. in high waves and/or strong winds, the deck of a ship can be inundated with water, which inundating water is typically designated "green water". It may damage ship and deck cargo and may be dangerous to people. Moreover, occurrences of green water on deck may be an expedient indication that the way in which the ship is conducted may be problematic and is therefore to be reviewed and optionally revised. Thus, when green water is found on the deck, it may not necessarily involve a major risk of damage to the cargo; but the presence of green water on the deck may thus be an indicator that changes should be performed in respect of the way in which the ship is conducted in order to reduce the risk of damage to the cargo due to the ship being conducted inexpediently. It will hence be advantageous to be able to detect the presence of water on the ship's deck. In particular, it would be advantageous if such detection were to take place continuously and/or even in case of small amounts of water, thereby enabling that any occurrence of green water be detected without delay.

It is not always possible to visually detect occurrences of water, if any, on the ship's deck from the bridge of e.g. large cargo vessels, such as container carriers, on the one hand due to the fact that there may be more than 200 m from bridge to stem and, on the other, due to the fact that the line of sight may be blocked by the cargo and also because the presence of water/inundations on the ship's deck is not a static situation; rather it may change continuously. It is not possible to post crew on the deck, since such measure could be fatal in rough weather conditions and, finally, sailing takes place at nighttime, too.

Owing to the powerful forces exerted by the inundating water and the weather in general, instrumentation, such as a video camera, on deck would be exposed to wear and a relatively high risk of damage.

It is an object of the invention to provide an apparatus for detecting occurrences of water on a ship's deck, wherein the apparatus is not exposed to substantial wear and/or damage when arranged on a ship in rough weather conditions.

This object is provided by an apparatus for detecting water on a ship's deck, wherein the apparatus comprises:
 a neutron source located below the surface of the ship's deck, and emitting fast/energy-rich neutrons; and
 a detector device located below the surface of the ship's deck and detecting thermal neutrons.

Hereby an apparatus is accomplished that is able to detect water through a non-modified and even non-perforated deck plate. The apparatus according to the invention uses the known knowledge to advantage that hydrogen, which is an element of water, is the elemental substance that most effectively of all elemental substances is able to brake neutrons with high kinetic energy. This effect is very marked, and hereby hydrogen distinguishes itself qualitatively from all other elemental substances with regard to braking neutrons, the so-called neutron-thermalisation. Hydrogen being a considerable element of water, and water typically being the only hydrogeneous material present on a ship's deck, and a deck plate of steel of a limited thickness absorbing essentially no neutrons, the apparatus will be able to detect water through the deck plate. Moreover, a detector device for detecting thermal neutrons will be able to provide a quick reaction, whereby the way in which the vessel is conducted can be subject to immediate review and optionally revision as a consequence of inundations of the ship's deck.

Thus, the apparatus according to the invention uses a neutron source for detecting water present on a ship's deck. A neutron source to this end is associated with the exemplary advantage that neutrons are able to penetrate certain barriers. For instance, it is possible by this invention to estimate the amount of water through a deck plate. Thereby it can be monitored whether and how much water is present on the ship's deck without having to e.g. modify or perforate the deck plate or portions thereof and Without having to locate the apparatus above deck where it would be exposed to the influences of the weather.

A fast-neutron source emits fast/energy-rich neutrons, i.e. neutrons with high kinetic energy. The present invention uses the known discovery to advantage that atomic nuclei (and hydrogen in particular) brake neutrons upon collision, which is typically designated "elastic scattering/collision" (whereby the speed is reduced and the direction changed for a collided neutron). This invention uses a detector device that detects relatively slow/energy-poor neutrons, the so-called thermal neutrons. After a neutron has been slowed down sufficiently it may be detected by the detector device.

According to a preferred embodiment the apparatus comprises further means for calibrating the apparatus by recording the intensity of thermal neutrons in known circumstances as a calibration value. It may be performed, e.g. when the deck has been painted or in connection with periodical controls.

It is a further object of the invention to provide an apparatus for detecting occurrences of water on a ship's deck, wherein the detection is accomplished continuously and/or even in case of small amounts of water, whereby an occurrence, if any, of green water on a ship's deck can be detected quickly.

This is accomplished in accordance with a preferred embodiment, wherein the apparatus according to the invention further comprises a moderator that is located below the surface of the ship's deck and brakes and reflects neutrons upon collision.

The process of braking down neutrons is typically designated "moderation" and a corresponding physical arrangement a "moderator". Most often, in order for a neutron to be detected, it must collide several times with hydrogen atoms. It is known to provide a detection apparatus with a moderator, an amount of hydrogen or a moderator material to accomplish an increased. sensitivity, wherein the moderator brakes and reflects/scatters neutrons by elastic scattering/ collision and is arranged such that an amount of incoming neutrons are reflected against the detector and the hydrogen to be detected. In broad outline, the further amount of hydrogen/moderator material acts as a (partial) neutron reflector that also slows down the neutrons, which means that an increased amount of braked/thermal neutrons will be detected. This is often also referred to as neutron "backscatter".

According to yet a preferred embodiment the apparatus further comprises:
 a light-emitting unit that emits light upon a nuclear-event/ reaction with a thermal neutron;
 a light-recording unit that emits an electrical pulse/an electrical signal upon registration of a flash of light;

wherein the moderator is a light-conductive unit provided between the light-emitting unit and the light-recording unit.

Hereby a water detector of improved sensitivity is accomplished, the light-conductive unit providing a conduction/concentration of the light from the light-emitting unit to the light-recording unit, which improves the efficiency/sensitivity further, whereby all the nuclear events that bring about a flash of light will, with a much improved reliability, be recorded by the light-recording unit.

Thus, the light-conductive unit serves a dual function, as—apart from conducting/concentrating the light, it also provides a moderating effect as it contains hydrogen/moderator material for achieving the above-referenced backscatter effect. This dual function of the light-conductive unit has the further effect that the apparatus according to the invention can be configured in a compact manner.

The improved sensitivity means that the used neutron source does not have to be so powerful that it constitutes a health hazard with ensuing requirements to safety equipment for an operator or cumbersome handling thereof, while simultaneously a reliable detection can still be provided through a deck plate, ie with modification, perforation or any other change to the deck plate. Moreover, due to the increased sensitivity and the further effect of the auxiliary moderator, smaller amounts of hydrogen and hence water amounts are detected compared to what would otherwise have been possible as it is otherwise difficult to detect small occurrences of hydrogeneous material/water due to the fact that a neutron has to achieve six to eight collisions in order to thermalised and hence be detectable by the detector device.

For instance, the light-emitting unit may be a scintillator, and a light-recording unit may be a photo-multiplier (PM). Alternatively the light-recording unit may be a photo-diode.

Particularly advantageously the source is arranged essentially in proximity of or in/around the centre of the face of said moderator that adjoins the light-emitting unit. This location has proved to be convenient to the effect that a further enhanced sensitivity is accomplished in that a larger amount of neutrons will be reflected and moderated and hence detected.

Also particularly advantageously, the light-emitting unit is configured essentially with a face adjoining the light-emitting unit and with a relatively smaller face bordering on a detecting face of the light-recording unit. Hereby a relatively larger face of the light-emitting unit can be coupled optically to a smaller detection face of the light recording unit, which yields an advantage with regard to economics, the cost of such light-recording units being comparatively high and depending very much on the recording area.

For instance, the light-conductive unit may be configured essentially as a cone with a cut-away top (i.e. a trapezoidal shape seen two-dimensionally, by a section through the centre line of the cone).

When the light-conductive unit of the apparatus is configured for emitting light guided from said light-emitting unit to the light-recording unit essentially perpendicular to a detection face, a particularly advantageous embodiment is accomplished, since a detection apparatus is hereby readily provided that has a larger expanse, essentially perpendicular to the deck plate on which the water to be detected is located. Hereby an advantageous configuration is accomplished, in particular if it is desired that the detection apparatus according to the invention is operated primarily in a depth direction.

According to an alternative embodiment, the light-conductive unit is configured for emitting light guided from the light-emitting unit to the light-recording unit, essentially in parallel with a detection face of the apparatus. In this manner a detection apparatus is readily provided that has a larger expanse essentially in parallel with a detection face of the object in which water is to be detected. In popular terms, the detection apparatus is longer than it is high. Hereby a particularly advantageous embodiment is accomplished, in particular if it is desired that the detection apparatus is comparatively flat, e.g. if it is mounted on the underside of the deck plate and if it is desired that it does not protrude too far below the declk plate.

According to yet a preferred embodiment of the apparatus, it further comprises an electric circuit connected to the detector device, wherein the electric circuit is configured for generating a signal that represents an estimated amount of water, wherein the generation is performed on the basis of the electrical signal from the light-recording unit.

The invention further relates to a method of detecting water on a ship's deck and comprising the following steps:
  emission of energy-rich neutrons from a neutron source that is located below the surface of the ship's deck; and
  detection of thermal neutrons by means of a detector device that is located below the surface of the ship's deck.

According to an embodiment of the method, the intensity of thermal neutrons in known circumstances is recorded as a calibration value. It is performed in particular during mounting of the apparatus.

According to yet an embodiment, the method further comprises a step of braking and reflecting neutrons upon collision by means of a moderator that is located below the surface of the ship's deck.

According to yet a further preferred embodiment the method comprises:
  emission of light from a light-emitting unit upon a nuclear eventreaction with a thermal neutron;
  emission of an electric pulse/an electrical signal by a light-recording unit upon registration of a flash of light; and
  conduction of light from said light-emitting unit to the light-recording unit by a light-conductive unit arranged between the light-emitting unit and the light-recording unit, wherein the moderator is the light-conductive unit.

Preferably, the light-conductive unit is configured for emitting light guided from said light-emitting unit to the light-recording unit essentially perpendicular to a detection face. Alternatively the light-conducting unit may be configured for emitting light guided from the light-emitting unit to the light-recording unit essentially in parallel with a detection face.

According to yet a preferred embodiment the method further comprises generation, in an electric circuit connected to said detector device, of a signal that represents an estimated amount of water, wherein said generation is performed on the basis of the electrical signal from the light recording unit.

The method according to the invention and its embodiments correspond to the apparatus according to the invention and embodiments thereof and have the same effects for the same reasons.

Figure 2A:
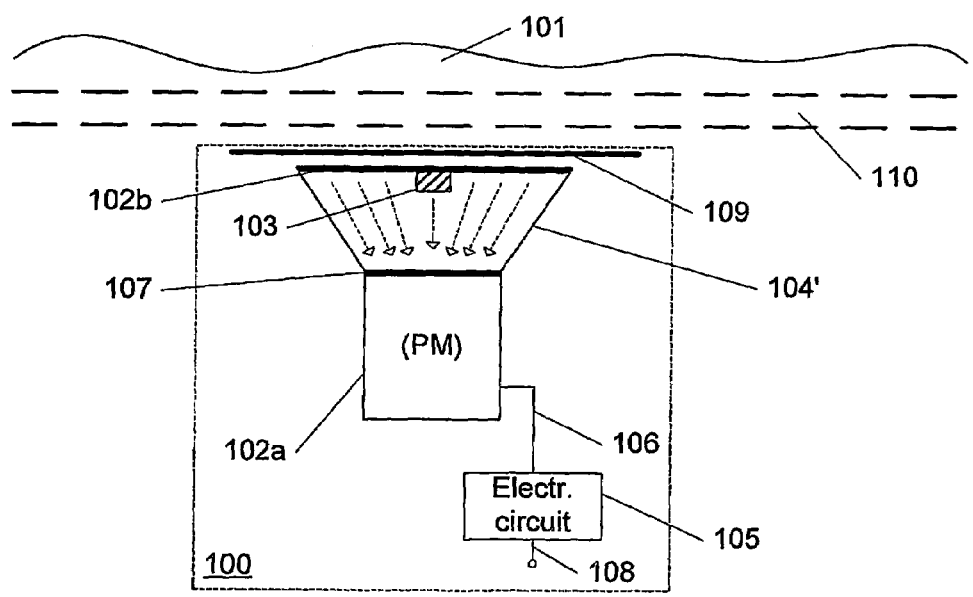
Figure 3:
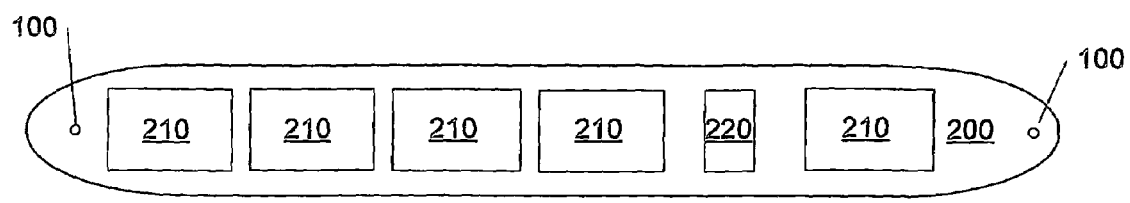

In the following the invention will be explained in further detail with reference to the drawing that shows exemplary embodiments of the invention, and wherein:

FIG. 1 illustrates an apparatus according to the invention located below a surface of a ship's deck, and wherein occurrences of water may be present on the deck plate of the ship's deck;

FIG. 2a schematically shows an embodiment of an apparatus according to the invention;

FIG. 2b schematically shows a second embodiment of an apparatus according to the invention;

FIG. 2c schematically shows a third embodiment of an apparatus according to the invention; and FIG. 3 schematically shows a vessel, seen from above, with cargo, bridge and the arrangement of a number of apparatuses according to the invention.

FIG. 1 illustrates an apparatus according to the invention arranged below the surface of a ship's deck, wherein an occurrence of water may be present on the decks plate (110) of the ship's deck. The drawing shows a deck plate (110), where the water to be detected is arranged above the deck plate (110) of the ship's deck, and wherein a detection apparatus (100) for detecting water (101) located on a ship's deck is arranged below the surface of the ship's deck. The detection apparatus (100) being located below the surface of the ship's deck, it follows that it is not exposed to weather conditions, such as wind, rain, sleet or the like. The detection apparatus (100) comprises a detector device (102) that detects thermal neutrons, and a neutron source (103) that emits fast/energy-rich neutrons (111). In the Figure, the detection apparatus (100) is shown arranged below the deck plate (110) as such; of course, it is also an option to arrange the detection apparatus (100) in a recess in the deck plate as such so as to protrude as little as possible from the lower face of the deck plate (110). What matters is that the entire detection apparatus (100) is located below the upper surface of the ship's deck.

Neutrons (111) emitted by the source (103) will go in essentially all directions and some of these neutrons will collide with the hydrogen that is a constituent of water (101), if any, on the ship's deck, whereby the neutrons will change direction and lose speed. A part of the neutrons will be reflected towards the detector device (102) for detection of thermal neutrons, and when they have collided a sufficient number of times, they will be thermal (ie typically have a kinetic energy of about approximately 0.025 eV), whereby the detector will record them and the amount of water (101) can be detected. Some neutrons will continue in other directions and/or be absorbed. Typically a neutron has to collide in average about 6 to 8 times with a hydrogen atom to possess energy that the detector is able to detect (the neutron must go down about six to eight values in energy level).

If the detector apparatus comprises a moderator (not shown) the moderator provides the effect that a larger number of neutrons with suitable energy will be detected compared to the scenario where only water (101) was primarily present for reducing the kinetic energy of the neutrons. Hereby the sensitivity of the detection apparatus (100) is enhanced.

FIG. 2a schematically illustrates an embodiment of an apparatus (100) according to the invention. In the Figure, a detection apparatus (100) is shown that comprises a neutron source (103) and a neutron-braking and -reflecting material (104'), ie a moderator material that comprises eg hydrogen. The detection apparatus (100) has a detecting face (109) that is intended to face in a direction towards an object (101), herein any occurrences of water to be detected. That is, the detecting face (109) of the detection apparatus (100) can be arranged to adjoin e.g. the lower face of the deck plate (110) of the ship's deck.

Moreover, the detection apparatus (100) further comprises a detector of thermal neutrons (102a, 102b), which detector according to the invention comprises a light-emitting unit (102b) and a light-recording unit (102a), wherein the light-recording unit (102a) is connected to an electric circuit (105). The light-emitting unit (102b) emits light in case of a nuclear event/reaction with a thermal neutron, while the light-recording unit (102a) emits an electric pulse/ an electrical signal (106) upon registration of a flash of light, where the emitted electric pulse/the emitted electrical signal is received in the electric circuit (105) for subsequent interpretation, processing, etc. The electric circuit (105) may furthermore contain means for calibrating the apparatus as described below.

According to the invention the moderator material is a light-conductive unit or a light conductive material (104'). In this manner the light-conductive unit (104') provides a dual function, since—as mentioned above—in addition to conducting/concentrating the light from the light-emitting (102b) unit to the detection face (107) of the light-recording unit (102a)—it also provides a moderating effect as it contains hydrogen/moderator material for achieving the above-referenced back-scatter effect. The light-conducting/-concentrating effect improves the efficiency/sensitivity, since the nuclear events that bring about a flash of light will, with much improved reliability, be recorded by the light-recording unit (102a), whereby smaller amounts of hydrogen may be detected without the strength of the neutron source having to be increased.

The movement of the light from the light-emitting unit (102b) to the light-recording unit (102a) is given schematically by dotted arrows in the Figure.

Moreover the dual function of the light-conductive unit/ moderator (104') causes the detection apparatus (100) to be configured compact or at least not larger than solutions that already comprise an auxiliary moderator for accomplishing neutron back-scatter.

In the shown embodiment the light-conductive unit (104') is configured essentially with a face bordering on the light-emitting unit (102b) and having a relatively smaller face bordering on a detection face (107) of the light-recording unit (102a). Hereby a relatively larger face of the light-emitting unit (102b) can be coupled optically to a smaller detection face (107) by the light-recording unit (102a), which yields a financial advantage as the cost of such light-recording units (102a) is relatively high and depends largely on the recording area. For instance, the light-conductive unit can be configured essentially as a cone where the top is cut away (ie a trapezoidal shape, seen two-dimensionally, by a section in the centre line of the cone).

The light-conducting unit/the light-conductive material (104') may be eg a light guide (GB term) comprising hydrogen and/or other moderator material. According to a preferred embodiment the light-conductive unit/the light-conductive material (104') is plexi-glass.

Preferably the neutron source (103) is comprised by/embedded in the moderator (104') and is arranged essentially around or centrally of the face of the moderator (104') that abuts on the light-emitting unit (102b). This arrangement has proved to be convenient in that a further enhanced sensitivity is accomplished in that a larger number of neutrons will be reflected and moderated and hence detected.

According to one embodiment the light-emitting unit (102b) is a scintillator, which is a known standard unit that records a nuclear event and emits a flash of light, when e.g. a thermal neutron hits the scintillator (102b). In practice, photons are released. One example of a scintillator (102b) is glass enriched with the lithium isotope Li-6.

According to one embodiment the light-recording unit (102a) is a photo-multiplier, which is also a known standard unit that records even very weak flashes of light/photons and generates an electric pulse on the basis of one or more of such. Alternatively the light-recording unit (102a) is a photo-diode.

The electric circuit (105) receives electric pulses/signals from the light-recording unit/the photo-multiplier (102a) and is thus able to record and/or process these signals in dependence on the current use, eg for estimating occurrences of water (101) or for other applications. For instance, one or more electric output signals (108) from the electric circuit (105) can be used for eg a display/meter (not shown) that shows the estimated amount and/or other functions.

Moreover, the detection apparatus (100) may comprise other types of light-conducting material (104') (optionally non-hydrogeneous materials, such as glass). The other types of light-conductive material may have a neutron-moderating effect; however, this is not a requirement unless it is essential that the detection apparatus is able to detect small amounts of water.

Preferably the light-recording unit the photo-multiplier (102a) and the light guide (104) will collide against/towards each other at the detection face (107) of the light recording unit/the photo-multiplier (102a) with an optic adaptation material there between, e.g. silicon grease, transparent silicon sealing compounds, etc, to ensure the lowest possible optical loss at the transition.

The neutron source (103) may be e.g. an isotope-based neutron source.

Alternatively the neutron source (103) may also be located in other places than in/around the centre of the light guide (104').

The electric circuit (105) may serve many functions and have many configurations depending on the relevant use of the invention. For instance, a simple electric circuit needs merely to record the number of electric pulses from the photomultiplier/the light-recording unit (102a) for a period of time in order to be able to estimate the amount of hydrogen/water in a simple manner. Alternatively, more advanced electric circuits may be used.

Furthermore, the apparatus (100) may comprise a material disc, plate, element, etc, (not shown) arranged such that the neutron source (103) is located between that and the detection face (109). Said disc, plate, element, etc, must be of a material that possesses the property that it is good at reflecting neutrons without significant loss of energy, e.g. iron or molybdenum. Moreover, the apparatus (100) may comprise a ring, tube, cylinder, etc, arranged to encircle the neutron source (103) whereby gamma radiation, if any, is removed that may otherwise provide false indications upon reaction with the light-emitting unit (102b). This ring, tube, cylinder, etc. may otherwise give false indications upon reaction with the light-emitting unit (102b). This ring, tube, cylinder, etc, has to be of a material that has the property that it absorbs gamma radiation in particular, e.g. lead or wolfram.

FIG. 2b schematically illustrates an alternative embodiment of an apparatus according to the invention. The Figure shows a detection apparatus (100) according to the invention comprising the same elements/units that are shown in and explained in connection with FIG. 2a, but arranged and optionally configured differently. More specifically, the combined moderator and light-conductive unit (104") is configured such that it guides the light essentially in parallel with the detection face (109) of the detection apparatus (100) to the light-recording unit (102a) (opposite the embodiment shown in FIG. 2a, where the light is guided essentially perpendicular to the detecting face (109)), which enables a rather elongate configuration of the detection apparatus (100). The light-conductive unit (104") may e.g., as indicated in the figure, be configured with a two-dimensional profile such as a triangle, where the incoming light from the light-emitting unit (102) is reflected essentially perpendicularly in relation to the ingoing direction, ie essentially in parallel with the detection face (109).

Alternatively the light-conductive unit (104") may be a batch of optical fibres/optical fibre cables that angles/turns/deflects the light sideways relative to the primary direction of incidence, i.e. essentially in parallel with the detection face (109).

The movement of the light from the light-emitting unit (102b) to the light-recording unit (102a) is shown schematically with dotted arrows in the Figure.

In the embodiment shown the light-conductive unit (104") is configured essentially with a face bordering on the light-emitting unit (102b) and having a relatively small face adjoining a detection face (107) of the light-recording unit (102a).

Hereby an elongate configuration is accomplished which is particularly advantageous in case it is desired to provide a comparatively flat detection apparatus (100), e.g. if it is mounted on the underside of the deck plate (110) and it is desired that it does not protrude too far down from the deck plate.

FIG. 2c schematically illustrates an alternative embodiment of an apparatus according to the invention. The shown embodiment corresponds to the one shown in FIG. 2a, the location of the neutron source (103) being changed, however. In the shown embodiment, the neutron source (103) is configured further towards the centre of the moderator (104'), i.e. not in the face of the moderator (104') that borders on the light-emitting unit (102b). Alternatively the neutron source (103) can be arranged e.g. further in the direction of one of the sides of the moderator (104').

In case only one detection apparatus is used, the obvious choice would be to arrange it at the foredeck; however, in case of detection of water on a ship's deck (200) it is, of course, possible to use several detection apparatuses (100), each of which is arranged below the upper face of the ship's deck, distributed across the ship's deck (200) in several places at a time by means of several apparatuses. FIG. 3 shows schematically an example of a ship seen from above, with a ship's deck (200) with cargo (210), a bridge (220) and a number of detection apparatuses (100) according to the invention. FIG. 3 shows two detection apparatuses; however, it will be understood that it is possible to use any desired number of detection apparatuses, depending on eg the size and type of the ship, previous experiences with occurrences of green water, etc. Typically detection apparatuses are arranged foremost on the ship's deck, however.

The detection apparatus according to the invention is preferably configured with means (105) for calibrating the apparatus by recording the intensity of thermal neutrons in known circumstances as a calibration value that is stored in a suitable memory unit for later retrieval for use in comparison with detection values. This calibration value can be deducted from the signal that estimates the amount of water material in order to thereby enable achievement of a more precise estimate for the amount of hydrogen deriving from water on the ship's deck. These means may comprise e.g. a button on the detection apparatus, wherein this button may be activated e.g. when the ship's cargo is taken onboard, thereby taking into account any sources of error. Such sources of error, if any, could be hydrogeneous materials in bulk-quantities in the cargo, radioactive material in proximity of the detection apparatus. Moreover, care can be taken to perform the calibration when the deck plate is essentially free from water, snow and ice, to the effect that the calibrated value for this state is recorded for use in the calculation of the amount of hydrogeneous material in case of occurrences of water. It is particularly convenient to perform the calibration upon mounting of the apparatus.

Typically, the detection apparatus according to the invention will be configured with a housing (not shown in the figures). This housing can advantageously be configured such that it has a neutron-reflecting effect, eg by use of iron. Of course, this adds increased weight compared to other—lighter—materials. Since, however, the importance of increased weight of an apparatus to be mounted on the underside of a ship's deck is insignificant, iron can thus advantageously be used with the ensuing advantages that iron provides.

Below, it will be explained how the detection apparatus can be used for recording the amount of water on a ship's deck. When no water is present on the deck, the detection apparatus will have a reading which is essentially the result of gamma radiation from the neutron source. Thus, this reading will be constant. Green water, i.e. water from inundations of the ship's deck, e.g. when travelling in high waves, will be displayed as periods of briefer duration with higher readings. Icing or snow, if any, that deposit on the deck will also be detected and will display as a reading that increases with the thickness of the ice/snow layer, but is otherwise constant. Therefore, green water on top of an ice layer could be detected as a detection of a given value that does not go below an increased value, but being, for a rather brief period, increased in relation to that increased value. It has been found that the apparatus will be able to detect icing and will be able to detect green water on top of a layer of ice or snow of up to at least 80 mm.

It was mentioned that essentially a deck plate of steel of limited thickness does not absorb the neutrons, and therefore the apparatus will be able to detect water through the ship's deck. It should be pointed out that the apparatus and the method according to the invention are not limited to use in connection of deck plates of steel; rather it may be adapted for use in connection with other deck materials, e.g. glass-fibre reinforced polyester or other. The contents of hydrogen in glass-fibre reinforced polyester, however, will reduce the sensitivity of the detection apparatus.

The electric circuit of the detection apparatus needs to correct for decay of the neutron source, which is both well known and simple. If for instance a Californium source is used, replacement at suitable intervals, eg every four years, is to be expected. The apparatus containing radioactive sources being subject to periodical controls under most national laws, eg at two-yearly intervals, replacement of the neutron source could be combined with such periodical control. Moreover, complete corrections could be made for electronic operation of the detection apparatus, whereby the reading of the detection apparatus would become very reliable.

The term "deck plate" is intended to designate the plate as such that separates the ship's deck, i.e. the level situated above the deck plate, from the level, e.g. cargo hold or intermediate deck, located below the ship's deck. The terms "upper face of ship's deck" are intended to designate the upwardly facing surface of the deck plate, while the term "on a ship's deck" is to be understood synonymously with the meaning "above the upper surface of the deck plate". That something is found below the surface of the ship's deck is to be understood such that it is contained below the upper face of the deck plate, i.e. does not protrude upwards through the deck plate, but, conversely, is entirely below the deck plate or is optionally situated partially embedded in the deck plate, e.g. in a recess in the downwardly facing face of the deck plate. It is implicit that the term "water" covers both "fresh water" and "sea water" and that the detection of the presence of water on the ship's deck is independent of whether the water is fresh water or sea water and independent of pollutants, if any, in the water.

The invention claimed is:

1. An apparatus (100) for detecting water on a ship's deck (110), where that the apparatus comprises:
    a neutron source (103) located below the surface of the ship's deck (110), and emitting fast/energy-rich neutrons (111); and
    a detector device (102, 102a, 102b) located below the surface of the ship's deck (110) and detecting thermal neutrons,
characterized in that the apparatus further comprises:
    a light-emitting unit (102b) that emits light upon a nuclear event/reaction with a thermal neutron;
    a light-recording unit (102a) that emits an electrical pulse or an electrical signal (106) upon registration of a flash of light; and
    a moderator (104', 104") that is located below the surface of the ship's deck (110) and brakes and reflects neutrons upon collision;
wherein the moderator (104'; 104") is a light-conductive unit provided between the light-emitting unit (102b) and the light-recording unit (102a).

2. An apparatus (100) according to claim 1, characterised in that the apparatus further comprises means (108) for calibrating the apparatus by recording the intensity of thermal neutrons in known circumstances as a calibration value.

3. An apparatus (100) according to claim 1, characterised in that the light-conductive unit (104") is configured for emitting light guided from said light-emitting unit (102b) to the light-recording unit (102a) essentially perpendicular to a detection face (109).

4. An apparatus (100) according to claim 1, characterised in that the light-conducting unit (104") is configured for emitting light guided from the light-emitting unit (102b) to the light-recording unit (102a), essentially in parallel with a detection face (109).

5. An apparatus (100) according to claim 1, characterised in that the apparatus further comprises an electric circuit (105) connected to the detector device (102; 102a), which electric circuit (105) is configured for generating a signal (108) that represents an estimated amount of water, wherein the generation is performed on the basis of the electrical signal (108) from the light-recording unit (102a).

6. A method of detecting water on a ship's deck (110), comprising the following steps:
    emission of energy-rich neutrons (111) from a neutron source (103) that is located below the surface of the ship's deck (110); and
    detection of thermal neutrons by means of a detector device (102; 102a; 102b) that is located below the surface of the ship's deck (110), characterized in that the method further comprises the following:
    emission of light from a light-emitting unit (102b) upon a nuclear event/reaction with a thermal neutron;
    emission of an electric pulse or an electrical, signal (106) by a light-recording unit (102a) upon registration of a flash of light;
    conduction of light from said light-emitting unit (102b) to the light-recording unit (102a) by a light-conductive unit arranged between the light-emitting unit (102b)

and the light-recording unit (102*a*), wherein the moderator (104'; 104") is the light-conductive unit; and braking and reflecting neutrons upon collision by means of a moderator (104'; 104") that is located below the surface of the ship's deck (110).

7. A method according to claim 6, characterised in that the intensity of thermal neutrons in known circumstances is recorded as a calibration value.

8. A method according to claim 6, characterised in that the light-conductive unit (104") is configured for emitting light guided from said light-emitting unit (102*b*) to the light-recording unit (102*a*) essentially perpendicular to a detection face (109).

9. A method according to claim 6, characterised in that the light-conducting unit (104") is configured for emitting light guided from the light-emitting unit (102*b*) to the light-recording unit (102*a*) essentially in parallel with a detection face (109).

10. A method according to claim 6, characterised in that the method further comprises generation, in an electric circuit (105) connected to said detector device (102; 102*a*), of a signal (108) that represents an estimated amount of water, wherein said generation is performed on the basis of the electrical signal (106) from the light recording unit (102*a*).

* * * * *